United States Patent [19]

Keifer et al.

[11] Patent Number: 4,909,831

[45] Date of Patent: Mar. 20, 1990

[54] SAFENING OF CROPS AGAINST A TRIAZOLINONE HERBICIDE WITH 1,8-NAPHTHALIC ANHYDRIDE

[75] Inventors: David W. Keifer, Skillman; John M. Tymonko, Hamilton Square, both of N.J.

[73] Assignee: FMC Corporation, Philadelphia, Pa.

[21] Appl. No.: 307,443

[22] Filed: Feb. 6, 1989

[51] Int. Cl.$^4$ ............................................ A01N 43/04
[52] U.S. Cl. ............................................ 71/92; 71/88
[58] Field of Search ...................................... 71/92, 88

[56] References Cited

U.S. PATENT DOCUMENTS 3,564,768  2/1971  Hoffman et al. ...................... 47/57.6
4,343,649  8/1982  Sweetser.

FOREIGN PATENT DOCUMENTS 0184870  6/1986  European Pat. Off.
WO87/03782  7/1987  PCT Int'l Appl.

OTHER PUBLICATIONS

Gulf Oil Chemicals Company, Product Bulletin "Protect®, Corn Seed Protectant" (1973).
C. Parker, "Herbicide Antidotes—A Review", Pestic. Sci., 14, 40–48 (1983).
O. C. Burnside, G. A. Wicks, C. R. Fenster, "Protecting Corn from Herbicide Injury by Seed Treatment" Weed Science 19, Issue 5, 565–568 (1971).
F. Y. Chang, G. R. Stephenson, J. D. Bandeen, "Comparative Effects of Three EPTC Antidotes", Weed Science, 21, Issue 4, 292–295 (1973).
F. W. Roeth, "Johnsongrass Control in Corn with Soil Incorporated Herbicides", Weed Science, 21, Issue 5, 474–476 (1973).
K. K. Hatzios, P. Zama, "Physiological Interactions Between the Herbicide EPTC and Selected Analogues of the Antidote Naphthalic Anhydride on Two Hybrids of Maize", Pestic. Sci., 17, 25–32 (1986).
O. P. Gupta, N. K. Niranwal, "Increasing Herbicide Selectivity in Maize and Cowpeas by Seed Treatment with Activated Carbon and NA" PANS, 22, No. 1, 86–89 (1976).
R. E. Holm, S. S. Szabo, "Increased Metabolism of a Pyrrolidine Urea Herbicide in Corn by a Herbicide Antidote" Weed Research, 14, 119–122 (1974).
A. M. Blair, M. L. Dean, "Improvement in Selectivity of Perfluidone against Rottboellia Exaltata in Maize with Herbicide Protectants", Weed Research, 16, 47–52 (1976).
J. R. C. Leavitt, D. Penner, "Potential Antidotes against Acetanilide Herbicide Injury to Corn (Zea Mays)", Weed Research, 18, 281–286 (1978).
K. K. Hatzios, D. Penner, "Potential Antidotes against Buthidazole Injury to Corn (Zea mays)", Weed Science, 28, issue 3, 273–276 (1980).
K. K. Hatzios, "Interactions between Selected Herbicides and Protectants on Corn (Zea mays)", Weed Science, 32, issue 1, 51–58 (1984).
W. T. Henry, K. K. Hatzios, "Interactions between the Herbicide Isouron and Selected Antidotes on Two Corn Hybrids", Cereal Research Communications, 13, No. 4, 421–427 (1985).
R. A. Schwartzbeck and O. L. Hoffmann, "Alleviation of EPTC Injury to Corn with 1,8-Naphthalic Anhydride", Proceedings Northeast Weed Science Soc., 27, 56 (1973).
C. Parker, W. G. Richardson, and T. M. West, "Potential for Extending the Selectivity of DPX 4189 by Use of Herbicide Safeness", Proceedings of The 1980 British Crop Protection Conference—Weeds, vol. 1, 15–22 (1980).
R. A. Peters, W. M. Dest, "Seed Treatment and Incorporation as Factors Influencing Annual Grass Control in Corn-1970", Proceedings of The Northeast Weed Science Soc., 25, 39–41 (1971).
K. K. Hatzios, "Herbicide Antidotes: Development, Chemistry, and Mode of Action", Advances in Agronomy, vol. 36, 265–315 (1983).

Primary Examiner—Catherine L. Mills
Attorney, Agent, or Firm—Beverly K. Johnson; Robert M. Kennedy; H. Robinson Ertelt

[57] ABSTRACT

Crops such as corn and other gramineous plants are protected from phytotoxic injury by the herbicide, 1-[2,4-dichloro-5-(N-methylsulfonylamino)phyenyl]-3-methyl-4-difluoromethyl-$\Delta^2$-1,2,4-triazolin-5-one, by coating the seeds of the crops, prior to planting, with a nonphytotoxic quantity of 1,8-naphthalic anhydride. The crops are safened against phytotoxic injury when the herbicide is applied pre-emergent, post-emergent or in a pre-plant incorporated manner.

26 Claims, No Drawings

SAFENING OF CROPS AGAINST A TRIAZOLINONE HERBICIDE WITH 1,8-NAPHTHALIC ANHYDRIDE

TECHNICAL FIELD

This invention relates to the control of undesirable vegetation encountered in the cultivation of various plant species, particularly agronomic crops.

BACKGROUND OF THE INVENTION

U.S. patent application Ser. No. 946,667, filed 12/31/86, allowed but not yet issued (issue fee paid) and corresponding PCT International Application No. WO87/03782, published 7/2/87, disclose triazolinone compounds which exhibit herbicidal activity, at low application rates, against a broad spectrum of grassy and broadleaf weeds. One such disclosed triazolinone compound which is very effective and commercially attractive as a preemergent herbicide in soybeans is 1-[2,4-dichloro-5-(N-methylsulfonylamino)phenyl]-3-methyl-4-difluoromethyl-$\Delta^2$-1,2,4-triazolin-5-one, hereinafter referred to as "Compound A," which has the structural formula

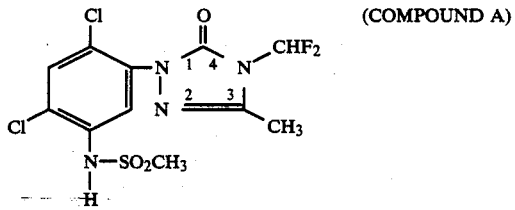

(COMPOUND A)

Although soybeans exhibit a tolerance to this herbicide, gramineous crops may suffer harmful phytotoxic effects when the herbicide is applied at rates effective to control undesired vegetation. Typical gramineous crops sensitive to effective weed-controlling rates of application of Compound A are corn, wheat, barley, rice and sorghum.

Compound A can be, and will be, sold with suitable instructions to prevent exposure to sensitive crops. However, measures which increase the tolerance of desirable plants to this herbicide without substantial diminution of herbicidal efficacy against weeds, will greatly expand the applicability as well as the commercial potential of this herbicide.

In this specification the term "crops" includes not only agronomic crops but plants of all kinds, and the term "gramineous" includes both cereal and non-cereal grassy crops, such as corn, wheat, oats, barley, rice, cotton, sorghum, and sugar cane.

SUMMARY OF THE INVENTION

It has now been found that crops, in particular gramineous crops, heretofore damaged by the application of Compound A to the locus of said crops, may be safened against the phytotoxic effects of the herbicide by treatment of the seeds of said crops, prior to planting, with 1,8-naphthalic anhydride. The discovery thereby permits the use of this herbicide to control weeds in crops in addition to soybeans and eliminates or substantially diminishes the risk of injury to the crops by drift of the herbicides to fields adjacent to a soybean stand or by rotation of a previously treated soybean field to another crop.

DETAILED DESCRIPTION

Compound A may be synthesized as described in U.S. patent application Ser. No. 946,667 and PCT International Application No. WO87/03782 mentioned above and exemplified in the Example below.

In general, the hydrazine portion of 2,4-dichlorophenylhydrazine is modified to form a triazolinone ring by reaction with pyruvic acid (forming the hydrazone) and then with a phosphoryl azide. Thereafter the 2,4-dichlorophenyl moiety of the intermediate is nitrated at its C-5 position and the nitro group is reduced to form an amino group, which is then treated with $CH_3SO_2Cl$ to convert the amino group to an $-N(SO_2CH_3)_2$ group. The compound having the $-N(SO_2CH_3)_2$ group may then be treated with a base such as NaOH to form the corresponding $-NR^1SO_2CH_3$ group, where $R^1$ is a salt-forming group (e.g. Na); this may then be treated with an acid to form the corresponding (acidic) $-NHSO_2CH_3$ group.

The following Example illustrates the preparation of Compound A (1-[2,4-dichloro-5-(N-methylsulfonylamino)phenyl]-3-methyl-4-difluoromethyl-$\Delta^2$-1,2,4-triazolin-5one). "$\Delta^2$-1,2,4-triazolin-5-one" used herein is synonymous with "dihydro-1,2,4-triazol-5(1H)-one."

EXAMPLE

Synthesis of Compound A

Step A Synthesis of Pyruvic Acid, 2,4-Dichlorophenylhydrazone as an Intermediate To a stirred solution of 16.2 g (0.07 mole) of commercially available 2,4-dichlorophenylhydrazine hydrochloride in 100 ml of ethanol was added in one portion 9.2 g (0.11 mole) of pyruvic acid in 100 ml of water. The reaction mixture was stirred for 10 minutes, and the resultant solid collected by filtration to yield when dried 13.5 g of pyruvic acid, 2,4-dichlorophenylhydrazone, m.p. 193°–194° C.

Step B Synthesis of 1-(2,4-Dichlorophenyl)-3-methyl-$\Delta^2$-1,2,4-triazolin-5-one as an Intermediate To a stirred suspension of 13.6 g (0.054 mole) of pyruvic acid, 2,4-dichlorophenylhydrazone in 100 ml of toluene was added 5.5 g (0.054 mole) of triethylamine. The reaction mixture became homogeneous, and 14.9 g (0.054 mole) of diphenylphosphoryl azide was added. Upon completion of addition the reaction mixture was heated to reflux where it was stirred for two hours. The reaction mixture was cooled to ambient temperature and extracted with 300 ml of aqueous 1N sodium hydroxide. The extract was neutralized with concentrated hydrochloric acid, and a solid precipitate was collected by filtration. The solid was washed with water and dried to yield 13.0 g of 1-(2,4-dichlorophenyl)-3-methyl-$\Delta^2$-1,2,4-triazolin-5-one; m.p. 174°–175° C.

Step C Synthesis of 1-(2,4-Dichlorophenyl)-3-methyl-4-difluoromethyl-$\Delta^2$-1,2,4-triazolin-5-one as an Intermediate A stirred solution of 16.0 g (0.065 mole) of 1-(2,4-dichlorophenyl)-3-methyl-$\Delta^2$-1,2,4-triazolin-5-one, 7.3 g (0.13 mole) of powdered potassium hydroxide, and 10.5 g (0.03 mole) of tetrabutylammonium bromide in 150 ml of tetrahydrofuran was cooled in an ice bath, and chlorodifluoromethane was bubbled into the reaction mixture. The ice bath was removed, and chlorodifluoromethane continued to bubble into the reaction mixture until condensation of it was observed on a dry ice condenser attached to the reaction vessel. Upon completion of addition the reaction mixture was stirred at ambient temperature for 16 hours. An additional 6.7 g (0.12 mole) of powdered potassium hydroxide was added to the reaction mixture, and it was again saturated with chlorodifluoromethane. The reaction mixtrre was stirred for two hours and then diluted with water. The mixture was extracted with diethyl ether, and the combined extracts washed with water. The organic layer was dried with sodium sulfate and filtered. The filtrate was concentrated under reduced pressure to a residue. The residue was dissolved in methylene chloride and passed through a pad of silica gel. The eluate was concentrated under reduced pressure to a residual solid. The solid was recrystallized from methylene chloride-heptane to yield 4.1 g of 1-(2,4-dichlorophenyl)-3-methyl-4-difluoromethyl-$\Delta^2$-1,2,4-tetrazolin-5-one as a solid, m.p. 108°–110° C.

Step D Synthesis of 1-(2,4-Dichloro-5-nitrophenyl)-3-methyl-4-difluoromethyl-$\Delta^2$-1,2,4-triazolin-5-one as an Intermediate To a stirred solution of 4.0 (0.013 mole) of 1-(2,4-dichlorophenyl)-3-methyl-4-difluoromethyl-$\Delta^2$-1,2,4-triazolin-5-one in 20 ml of concentrated sulfuric acid was slowly added 1.2 ml (0.015 mole) of 70% nitric acid, while maintaining the reaction mixture temperature at 25° C. Upon completion of addition the reaction mixture was stirred at 25° C. for 30 minutes and then poured into ice water. The resultant solid was collected by filtration. The solid was dissolved in methylene chloride and passed through a pad of silica gel. The eluate was subjected to column chromatography on silica gel. Elution was completed using 1:1 petroleum ether:-methylene chloride. The appropriate fractions were combined and concentrated under reduced pressure to yield 3.0 g of 1-(2,4-dichlorophenyl-5-nitrophenyl)-3-methyl-4-difluoromethyl-$\Delta^2$-1,2,4-triazolin-5-one; m.p. 95°–97° C.

Step E Synthesis of 1-(5-Amino-2,4-dichlorophenyl)-3-methyl-4-difluoromethyl-$\Delta^2$-1,2,4-triazolin-5-one as an Intermediate To a stirred solution of 2.5 g (0.007 mole) of 1-(2,4-dichloro-5-nitrophenyl)-3-methyl-4-difluoromethyl-$\Delta^2$-1,2,4-triazolin-5-one in 60 ml of acetic acid and 6 ml of water was added portionwise 2.5 g (0.045 mole) of powdered iron at a rate to maintain the reaction mixture temperature below 35° C. Upon completion of addition the reaction mixture was stirred at 25°–30° C. for two hours. The reaction mixture was diluted with diethyl ether with stirring and then was filtered through diatomaceous earth. The stirred filtrate was made basic with aqueous 10% sodium bicarbonate solution and solid potassium carbonate. The organic layer was separated, washed with three portions of water and then dried with sodium sulfate. The mixture was filtered, and the filtrate was concentrated under reduced pressure to a residue. The residue was purified by column chromatography on silica gel using methylene chloride:acetone as an eluent. The appropriate fractions were combined and concentrated under reduced pressure to yield 2.0 g of 1-(5-amino-2,4-dichlorophenyl)-3-methyl-4-difluoromethyl-$\Delta^2$-1,2,4-triazolin-5-one; m.p. 133°–135° C. The nmr and the ir spectra were consistent with the proposed structure.

Step F Synthesis of 1-[2,4-dichloro-5-[bis-(N-methylsulfonyl)amino]-phenyl]-3-methyl-4-difluoromethyl-$\Delta^2$-1,2,4-triazolin-5-one as an Intermediate A stirred solution of 1.2 g (0.004 mole) of 1-(5-amino-2,4-dichlorophenyl)-3-methyl-4-difluoromethyl-$\Delta^2$-1,2,4-triazolin-5-one and 0.95 g (0.009 mole) of triethylamine in 15 ml of methylene chloride was cooled in an ice/acetone bath, and 0.97 g (0.009 mole) of methanesulfonyl chloride was added dropwise at a rate to maintain the reaction mixture temperature below 0° C. The complete addition required five minutes. Upon completion of addition the reaction mixture was allowed to warm to ambient temperature where it stirred for 16 hours. After this time the reaction mixture was concentrated under reduced pressure to a residue. The residue was purified by column chromatography on silica gel using 50:1 methylene chloride:acetone as an eluent. The appropriate fractions were combined and concentrated under reduced pressure to a solid. The solid was recrystallized from acetone/heptane to yield 1.3 g of 1-[2,4-dichloro-5-[bis-(N-methylsulfonyl)amino]phenyl]-3-methyl-4-difluoromethyl-$\Delta^2$-1,2,4-triazolin-5-one; m.p. 213°–214° C.

The nmr spectrum was consistent with the proposed structure.

Analysis calc'd for
$C_{12}H_{12}C_{12}F_2N_4O_5S_2$: C 30.91; H 2.59; N 12.02; Found: C 31.15; H 2.43; N 12.03.

Step G Synthesis of Compound A

To a stirred solution of 0.8 g (0.002 mole) of 1-[2,4-dichloro-5-[bis-(N-methylsulfonyl)amino]phenyl]-3-methyl-4-difluoromethyl-$\Delta^2$-1,2,4-triazolin-5-one in 10 ml of ethanol was added a solution of 0.14 g (0.003 mole) of sodium hydroxide in 0.3 ml of water. Upon completion of addition the reaction mixture was stirred for 15 minutes and then was poured into 100 ml of water. The mixture was neutralized with concentrated hydrochloric acid, and the solid precipitate collected by filtration. The solid was dried to yield 0.5 g of Compound A, [1-[2,4-dichloro-5-(N-methylsulfonylamino)-phenyl]-3-methyl-4-difluoromethyl-$\Delta^2$-1,2,4-triazolin-5one]; m.p. 75°–78° C.

The nmr spectrum was consistent with the proposed structure.

Analysis calc'd for
$C_{11}H_{10}C_{12}F_2N_4O_3S$: C 34.21; H 2.59; N 14.51; Found: C 33.98; H 2.62; N 14.20.

In accordance with the method of the invention, crops are safened against the herbicide Compound A by coating, using conventional techniques, 1,8-naphthalic anhydride onto the surface of the seeds of crops to be protected prior to planting the seeds. The amount of 1,8-naphthalic anhydride applied is an amount sufficient to safen the crops from the phytotoxic effects of the herbicide. As will be obvious to the skilled artisan, safening amounts of 1,8-naphthalic anhydride will vary according to such factors as the plant to be protected, soil conditions, and the rate of application of the herbicide. Generally, the amount of 1,8-naphthalic anhydride used to treat or coat the seed should be at least about 0.05 to about 2%, e.g. 0.1 to 1%, preferably 0.25 to 1%, weight based on the weight of the seed treated with naphthalic anhydride, (wt/wt).

Compound A is formulated and applied in effective herbicidal amounts in accordance with procedures and standards in herbicidal treatment. Generally, the herbicide is applied in dilute form with an agriculturally acceptable, relatively inert, solid or liquid carrier to the locus where herbicidal effect is desired. Since, as is well known, the formulation and mode of application of an agricultural chemical may affect activity in a given application, the herbicide may be formulated as emulsifiable concentrates (EC's), as granules preferably of relatively large particle size, as wettable powders, as solutions or suspensions, or in other forms.

The herbicide is applied to the locus of the plant where control is desired in a preemergent or post-emergent manner, or in a pre-plant incorporated manner. When applied postemergent, the herbicide is preferably, applied shortly after the plant emerges. In all formulations, the herbicide is applied as the active ingredient alone or in a tank mix with other agricultural chemicals.

For preemergence application the herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both preemergence and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5% to 80% of active ingredient, depending on the absorbency of the carrier, and usually also contain a small amount of a wetting, dispersing or emulsifying agent to facilitate dispersion.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing, or emulsifying agents used in agricultural formulations include, for example, the alkyl and alkylaryl sulfonates and sulfates and their sodium salts, polyhydric alcohols, and other types of surface active agents, many of which are available in commerce. The surface active agent, when used, normally comprises 1% to 15% by weight of the herbicidal composition.

Other useful formulations for the herbicidal applications include simple solutions of the active ingredient in a solvent in which it is completely soluble at the desired concentration, such as acetone, alkylated naphthalenes, xylene, or other organic solvents. Thus a suitable solution may contain, for instance, some 65% of the active ingredient, together with a minor proportion (say 1 to 10%) of a surfactant; for use on the field, this solution may be diluted with water, by the farmer, to provide an aqueous composition containing, say about 0.25% to 1.5% of the active ingredient. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal applications of the present compounds. Such granular formulations are free-flowing, non-dusty, and readily water-soluble or water-miscible. The soluble or dispersible granular formulations described in U.S. Pat. No. 3,920,442 may be used to apply the herbicidal compounds. For use in the field, these formulations may be diluted with water by the farmer or applicator to provide an aqueous composition containing say 0.25% to 1.5% of the active ingredient.

The active herbicidal compound used in the method of the invention may be formulated and/or applied with insecticides, fungicides, nematicides, plant growth regulators, fertilizers, or other agricultural chemicals and be used an effective soil sterilant as well as a selective herbicide in agriculture. In applying the active compound, whether formulated alone or with other agricultural chemicals, an effective amount and concentration of the active compound is of course employed; the amount may be about 15 to 500 grams per hectare (g/ha), i.e. about 0.015 to 0.5 kilograms per hectare (kg/ha).

Herbicidal Evaluation

The herbicidal composition and safener of the invention were evaluated in a laboratory greenhouse as described below.

In conducting the following tests, Compound A was used as 1:1 acetone-water solutions containing 0.5% Tween 20 as the surfactant.

Tolerance of Crops Treated Preemergence with Compound a Using Seeds Coated with 1,8-Naphthalic Anhydride An appropriate amount of seeds of the targeted crops was placed in a clean, rotating drum mixer, and a sufficient amount of an aqueous 2% solution of sodium carboxymethylcellulose was added to provide a 2% (wt/wt) application of the sticker to the seeds. This mixture was rotated until the sticker solution was evenly distributed on the seeds. Aliquots of these seeds were then placed in a glass jar to which was added sufficient 1,8-naphthalic anhydride to provide the desired concentration of safener on the seeds. The lid was securely closed, and the jar was then rolled on its side at 160 rpm for 20 minutes on a machine with rubber rollers, coating the seed uniformly at the desired concentration. Concentrations of 1,8-naphthalic anhydride used were 0.05 and 0.25% (wt/wt).

Seeds of the following crops were used in the test: corn (*Zea mavs*), both Pioneer brand hybrid 3732 and Dekalb brand hybrid T1100, wheat (*Triticum aestivum*) (cvs. Wheaton and Batum), barley (*Hordeum vulgare*) (C. V. Henry), rice (*Oryza sativa*) (cvs. LaBelle and Mars), sorghum (*Sorghum vulgare*) (cv. Y200B), and oats (*Avena sativa*) (cv. Monida).

Six disposable fiber flats (8 cm × 15 cm × 25 cm) were filled to an approximate depth of 6.5 cm with a steam-sterilized sandy loam soil. The soil was leveled and impressed with a template that provided in each flat 15 evenly spaced furrows 13.3 cm long and 0.5 cm deep. One flat of each pair was planted with five rows of crops and the other with four rows of crops. Treated seeds were planted in three flats and untreated ones in the three remaining flats. The template was again employed to firmly press the seeds into the soil. A topping soil, prepared by mixing equal portions of sand and sandy loam soil, was placed uniformly on top of each flat to a depth of approximately 0.5 cm.

Six such flats were prepared for each rate of application of Compound A. Application rates of the herbicide were 0.015, 0.031, 0.062, 0.125, 0.25, and 0.50 kg/ha. Six flats were planted which received no application of herbicide, three with treated seed and three with untreated seed. Six flats were sprayed with each rate of application of herbicide. All flats were then placed in a greenhouse where they were watered at the soil surface for a period of fourteen days. At this time the phytotoxicity of Compound A to the plants from treated and untreated seed was recorded. Individual crop hybrids were examined for percent kill, and a vigor rating of one to five was assigned to the surviving plants, a vigor rating of five signifying no chemical injury and a vigor rating of one indicating severe injury. An injury rating using the percent kill and vigor rating for each corn hybrid in the test was calculated using the following formula:

Injury = percent Kill + X (100 percent kill)

| X = | Vigor 1 = | 1 |
|---|---|---|
| | Vigor 2 = | 0.75 |
| | Vigor 3 = | 0.25 |
| | Vigor 4 = | 0.12 |
| | Vigor 5 = | 0 |

Utilizing the injury ratings calculated, the increased tolerance of the test plants from seeds treated with 1,8-naphthalic anhydride compared to the test plants from untreated seeds was calculated in terms of percent reduction of injury using the following formula:

$$\text{Percent reduction of injury} = \frac{\text{Injury to crops from untreated seeds} - \text{Injury to crops from treated seeds}}{\text{Injury to crops from untreated seeds}} \times 100$$

(The foregoing method of determining injury and calculating reduction of injury were used in all subsequent tests described below).

As shown in Table I, appended, the greatest reduction to herbicidal injury generally occurred at the lowest rates of application and the least reduction at the highest rates of herbicidal application. Corn, wheat and barley were best protected from the phytotoxic effects of the herbicide by the treatments of 1,8-naphthalic anhydride. Sorghum and oats were less protected at the rates of application tested.

Tolerance of Corn Against Postermergence Treatment with Compound A Using Seeds Coated with 1,8-Naphthalic Anhydride This test was conducted similarly to the preemergence test above except corn seeds (Pioneer brand hybrid 3732) were treated with 0.5% (wt/wt) 1,8-naphthalic anhydride and application rates of the herbicide were 0.031, 0.063, 0.125, and 0.25 kg/ha. Also, two growth stages were achieved by planting treated seeds five and eleven days before herbicide application. The herbicide was sprayed postemergence in a spray volume of 280 1/ha. Injury ratings were calculated using the same formula as in the preemergence test above, but injury ratings were recorded four and fifteen days following herbicide application.

The results of the test showed that corn is safened against the phytotoxic effects of the herbicide postemergence when the seeds are coated with 1,8-naphthalic anhydride prior to planting. Safening is generally most effective when the herbicide is applied shortly after the plant emerges. As shown in Table 2, appended, the greatest and most persistent reduction in injury occurred when the herbicide was applied at the earlier growth stage. When the herbicide was applied at the later stage of growth, safening with 1,8-naphthalic anhydride was initially less effective and less persistent than when the herbicide was applied at the earlier growth stage.

TABLE 1

Reduction In Injury to Gramineous Crops Preemergent from Compound A[a] by Treatment of Seed with 1,8-Naphthalic Anhydride Percent Reduction of Injury[d]

| Application Compound A[b] | Rate of NA[c] | Corn DeKalb T1100 | Corn Pioneer 3732 | Wheat cv. Wheaton | Wheat cv. Batum | Barley Henry | Rice LaBelle | Rice Mars | Sorghum | Oats |
|---|---|---|---|---|---|---|---|---|---|---|
| 0.015 | 0.05% | −150 | 100 | 100 | 40 | 37.5 | 87.0 | 80.0 | 75.0 | 60.0 |
| 0.031 | 0.05% | −40 | 100 | — | −60 | 20.0 | 57.1 | 45.5 | 31.7 | 38.5 |
| 0.062 | 0.05% | 0 | 100 | 100 | 0 | 23.1 | 53.6 | −50 | 0 | 9.1 |
| 0.125 | 0.05% | 70.4 | 94.3 | 73.3 | 23.1 | 68.0 | 53.5 | −81.8 | 0 | 3.0 |
| 0.25 | 0.05% | 84.9 | 62.3 | 29.8 | 42.5 | 21.4 | 41.5 | 34.2 | 4.1 | 30.7 |
| 0.50 | 0.05% | 21.7 | −21.7 | 20.0 | 12.3 | 14.9 | 25.4 | −13.3 | 2.1 | −4.2 |
| 0.015 | 0.25% | −150 | 100 | 33.3 | 0 | 12.5 | 91.3 | 46.7 | 90.6 | 40.0 |
| 0.031 | 0.25% | 0 | 33.3 | — | 0 | 20.0 | 71.4 | 40.9 | 4.8 | 46.2 |
| 0.062 | 0.25% | −40 | 75.0 | 100 | 37.5 | 23.1 | 0 | −87.5 | 5.7 | 22.7 |
| 0.125 | 0.25% | 92.6 | 100 | 93.3 | 38.5 | 52.0 | 69.8 | −27.3 | 7.4 | −12.1 |

TABLE 1-continued

Reduction In Injury to Gramineous Crops Preemergent from Compound A[a] by Treatment of Seed with 1,8-Naphthalic Anhydride
Percent Reduction of Injury[d]

| Application Compound A[b] | Rate of NA[c] | Corn DeKalb T1100 | Corn Pioneer 3732 | Wheat cv. Wheaton | Wheat cv. Batum | Barley Henry | Rice LaBelle | Rice Mars | Sorghum | Oats |
|---|---|---|---|---|---|---|---|---|---|---|
| 0.25 | 0.25% | 90.6 | 90.6 | 68.1 | 67.5 | 64.3 | 56.9 | 0 | 7.2 | 29.3 |
| 0.50 | 0.25% | 78.3 | 41.7 | 37.7 | 43.9 | 35.8 | 15.9 | −17.3 | 4.1 | −11.1 |

[a]Compound A = 1-[2,4-dichloro-5(N-methylsulfonylamino)phenyl]methylsulfonylamino)phenyl]-3-methyl-4-difluoromethyl-$\Delta^2$-1,2,4-triazolin-5-one
[b]kg/ha (kilogram per hectare)
[c]Weight percent based on weight of seeds treated with 1,8-naphthalic anhydride

[d] Percent Reduction of Injury = $\dfrac{\text{Percent Injury of Unsafened Crop} - \text{Percent Injury of Safened Crop}}{\text{Percent Injury of Unsafened Crop}} \times 100$

TABLE 2

Reduction in Injury to Corn[a] Postemergent from Compound A by Treatment of Seeds with 1,8-Naphthalic Anhydride

| Application Compound A[b] | Rate of NA[c] | DAP[d] | Percent Reduction of Injury 4 DAT[e] | 15 DAT |
|---|---|---|---|---|
| 0.031 | 0.5 | 5 | 71.9 | 75.0 |
| 0.063 | 0.5 | 5 | 72.4 | 76.2 |
| 0.125 | 0.5 | 5 | 60.0 | 83.0 |
| 0.25 | 0.5 | 5 | 45.6 | 73.0 |
| 0.031 | 0.5 | 11 | 55.6 | 0 |
| 0.063 | 0.5 | 11 | 44.0 | 0 |
| 0.125 | 0.5 | 11 | 46.2 | 42.1 |
| 0.25 | 0.5 | 11 | 54.5 | 25.0 |

[a]Corn cultivar = Pioneer brand hybrid 3732
[b]kg/ha (kilogram/hectare)
[c]Weight percent based on weight of seeds treated with 1,8-naphthalic anhydride
[d]DAP = Days after planting
[e]DAT = Days after treatment with Compound A

We claim:

1. A method of protecting a gramineous crop from phytotoxic injury due to application in the locus thereof of a herbicidally effective amount of the herbicidal compound of the formula

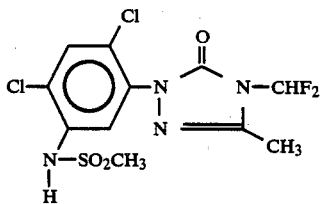

which method comprises applying to the seeds of the crop a non-phytotoxic antidotally effective amount of 1,8-naphthalic anhydride prior to planting the seeds.

2. The method of claim 1 wherein the herbicidal compound is applied to the soil prior to planting the seeds of the crop.

3. The method of claim 1 wherein the herbicidal compound is applied to the soil after planting of the seeds of the crop and prior to emergence of the crop.

4. The method of claim 1 wherein the herbicidal compound is applied to the soil after planting of the seed of the crop and after emergence of the crop.

5. The method of claim 1 wherein the gramineous crop is corn.

6. The method of claim 1 wherein the gramineous crop is wheat.

7. The method of claim 1 wherein the gramineous crop is barley.

8. The method of claim 1 wherein the gramineous crop is rice.

9. The method of claim 1 wherein the gramineous crop is sorghum.

10. The method of claim 2 wherein the gramineous crop is corn.

11. The method of claim 2 wherein the gramineous crop is wheat.

12. The method of claim 2 wherein the gramineous crop is barley.

13. The method of claim 2 wherein the gramineous crop is rice.

14. The method of claim 2 wherein the gramineous crop is sorghum.

15. The method of claim 3 wherein the gramineous crop is corn.

16. The method of claim 3 wherein the gramineous crop is wheat.

17. The method of claim 3 wherein the gramineous crop is barley.

18. The method of claim 3 wherein the gramineous crop is rice.

19. The method of claim 3 wherein the gramineous crop is sorghum.

20. The method of claim 4 wherein the gramineous crop is corn.

21. The method of claim 4 wherein the gramineous crop is wheat.

22. The method of claim 4 wherein the gramineous crop is barley.

23. The method of claim 4 wherein the gramineous crop is rice.

24. The method of claim 4 wherein the gramineous crop is sorghum.

25. The method of claim 1 wherein the herbicidal compound is applied to the locus of the gramineous crop in an amount of about 0.015 to about 0.5 kilogram per hectare.

26. The method of claim 1 wherein 1,8-naphthalic anhydride is applied to the seeds of the gramineous crop in an amount of about 0.05 to 1 percent weight based on the weight of the coated seed.

* * * * *

UNITED STATES PATENT AND TRADEMARK OFFICE
CERTIFICATE OF CORRECTION

PATENT NO. : 4,909,831

DATED : March 20, 1990

INVENTOR(S) : David W. Keifer and John M. Tymonko

It is certified that error appears in the above-identified patent and that said Letters Patent is hereby corrected as shown below:

Column 7, lines 43-44, "Injury = percent Kill + X(100 percent kill)" should read -- Injury = percent Kill + X(100-percent kill) --.

Signed and Sealed this

Fourteenth Day of July, 1992

Attest:

DOUGLAS B. COMER

*Attesting Officer*   *Acting Commissioner of Patents and Trademarks*